United States Patent [19]

Kontos

[11] Patent Number: 5,755,727
[45] Date of Patent: May 26, 1998

[54] METHOD DEVICE FOR LOCATING AND SEALING A BLOOD VESSEL

[75] Inventor: Stavros Kontos, Woodcliff Lake, N.J.

[73] Assignee: Cardiologics L.L.C., Totowa, N.J.

[21] Appl. No.: 459,853

[22] Filed: Jun. 2, 1995

[51] Int. Cl.⁶ ............................................. A61B 17/00
[52] U.S. Cl. ........................... 606/144; 606/139; 112/169
[58] Field of Search ........................... 606/139, 144, 606/145, 147, 148; 112/169, 80.03

[56] References Cited

U.S. PATENT DOCUMENTS

| | | |
|---|---|---|
| 4,744,364 | 5/1988 | Kensey . |
| 4,852,568 | 8/1989 | Kensey . |
| 4,890,612 | 1/1990 | Kensey .................................. 606/213 |
| 4,929,246 | 5/1990 | Sinofsky ................................... 606/8 |
| 5,021,059 | 6/1991 | Kensey et al. ........................ 606/213 |
| 5,053,046 | 10/1991 | Janese ................................... 606/215 |
| 5,061,274 | 10/1991 | Kensey .................................. 606/213 |
| 5,108,421 | 4/1992 | Fowler .................................. 606/213 |
| 5,304,184 | 4/1994 | Hathaway et al. ...................... 606/144 |
| 5,496,332 | 3/1996 | Sierra et al. .......................... 606/148 |
| 5,527,322 | 6/1996 | Klein et al. ........................... 606/145 |

*Primary Examiner*—Jeffrey A. Schmidt
*Attorney, Agent, or Firm*—Kenyon & Kenyon

[57] ABSTRACT

A device for locating and sealing a small incision or puncture in a blood vessel includes a housing with a plurality of openings formed therethrough. A plunger is slidably mounted in the housing and has a plurality of apertures formed therethrough. The apertures in the plunger are aligned with the openings in the housing. A tube extends through each of the aligned apertures and openings and accommodates a piercing stylet that extends through the tubes. A suture guide extends from one end of the housing for releasably retaining a suture therein.

4 Claims, 9 Drawing Sheets

METHOD DEVICE FOR LOCATING AND SEALING A BLOOD VESSEL

BACKGROUND OF THE INVENTION

The present invention relates generally to medical devices and, more particularly, toward a method and device for locating and sealing percutaneously formed punctures or incisions in a blood vessel.

A physician must frequently close openings that are formed in blood vessels during various intravascular procedures. The openings are generally formed in order to allow intravascular instruments such as catheters to be inserted into the vessel. Once the procedure is carried out, the opening (or openings) in the vessel is closed by applying and maintaining pressure on the skin until coagulation occurs. It is generally acknowledged that effectuating such closures is time consuming for the physician and painful to the patient.

Devices for sealing a punctured vessel wall with sutures are well known in the art. For example, U.S. Pat. No. 4,744,364 discloses a device for sealing a percutaneous puncture in a vessel that includes a tubular body with an expandable closure therein. The body also has an ejecting means that forces the closure out of the body into the interior of the blood vessel, whereupon the closure expands to form an engagement surface. A piece of thread is secured to the closure through the body so that the closure can be pulled toward the puncture in the vessel in order to seal the same. No means are provided for readily locating the puncture in the blood vessel. See, also, U.S. Pat. Nos. 4,852,568 and 4,890,612.

U.S. Pat. No. 5,053,046 discloses a spinal cannula that seals a puncture in the spine created by the cannula itself. The device includes a first cannula and a second cannula. The second cannula is inserted into the first and includes a dural seal with an absorbable suture extending therefrom. The first cannula effectuates the initial spinal puncture. Once the diagnostic or therapeutic procedure is accomplished, the second cannula is inserted into the first cannula until it extends through the puncture. A stylet is inserted into the inner cannula whereupon it pushes the seal and absorbable suture into the cerebrospinal fluid. The seal absorbs liquid and swells. The cannulae are removed and the physician then pulls on the suture in order to set the dural seal in the spinal puncture. While this device may be effective in sealing a puncture in a spine, it would not be effective for sealing an opening in a more flexible structure such as a blood vessel.

U.S. Pat. No. 5,021,059 discloses a plug device for sealing punctures in tissue. The device includes a carrier that has an anchoring portion, a sealing portion and a thin filament connected therebetween. The carrier has an end that is adapted to fit through the puncture. In use, the anchoring portion is ejected through the puncture and is then drawn toward the free end of the carrier. The instrument is manipulated in order to draw the anchoring portion against the puncture on the inner surface of the tissue. To completely seal the puncture, the instrument is further manipulated to draw the sealing portion into engagement with the outer surface of the tissue on the opposite side of the anchoring portion. This is a relatively complicated device that requires a great deal of manipulation on the part of the surgeon.

SUMMARY OF THE INVENTION

The present invention is designed to overcome the deficiencies of the prior art discussed above. It is an object of the invention to provide an arrangement for readily locating and sealing percutaneously formed punctures or incisions in a living being.

It is a further object of the invention to provide a device that is relatively simple to construct and is low in cost.

It is yet another object to provide such a device that is safe and efficient to use.

In accordance with the illustrative embodiments, demonstrating features and advantages of the present invention, there is provided a device for locating and sealing an incision or puncture in a blood vessel. The device comprises a housing that has a first segment and a second segment. The first segment has a plurality of openings formed therethrough. The second segment is substantially hollow. A plunger is slidably mounted in the second segment and has a plurality of apertures formed therethrough. Each opening is aligned with one of the apertures. A different tube extends through a corresponding one of the openings and apertures. Extending from the aperture and opening pairs, is a corresponding stylet that ends in a pointed tip. A suture guide is secured to and spaced from the end of the first segment of the housing and has a pair of openings for receiving each of the stylets.

Other objects, features and advantages will be readily apparent from the following detailed description of a preferred embodiment thereof taken in conjunction with the drawings.

BRIEF DESCRIPTION OF THE DRAWINGS

For the purpose of illustrating the invention, there are shown in the accompanying drawings forms which are presently preferred; it being understood that the invention is not intended to be limited to the precise arrangements and instrumentalities shown.

DETAILED DESCRIPTION OF THE PREFERRED EMBODIMENT

Figure 4:
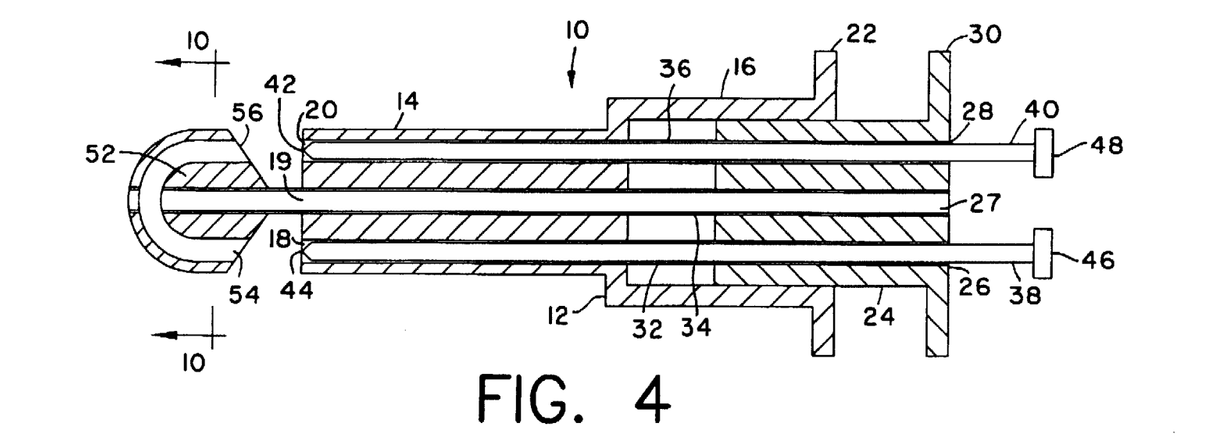
FIG. 4 is a side cross-sectional view of the present invention.
Figure 5:
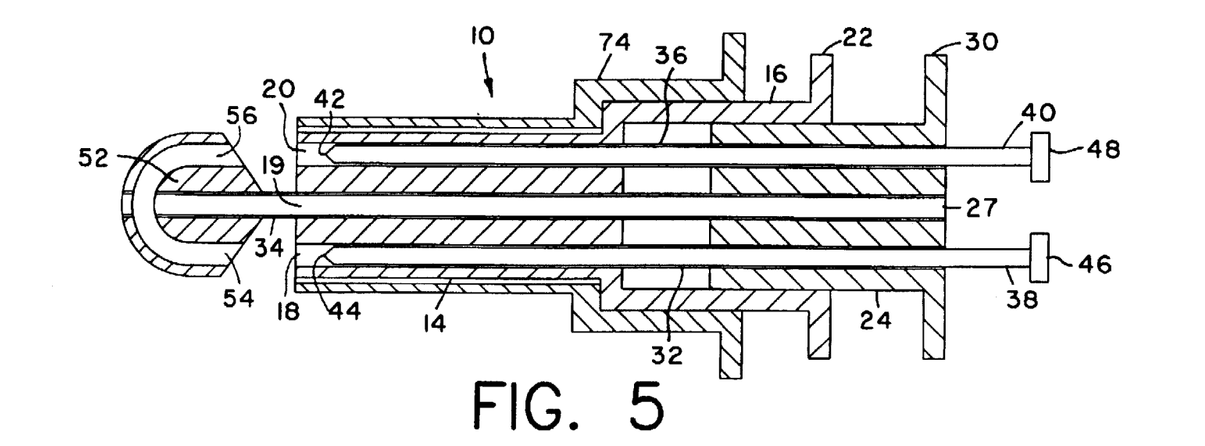
FIG. 5 is a side cross-sectional view of the present invention inserted into the procedure sheath.

Referring now to the drawings in detail wherein like reference numerals have been used throughout the various figures to designate like elements, there is shown in FIG. 4 a device for locating and sealing percutaneous incisions or punctures in a blood vessel constructed in accordance with the principles of the present invention and designated generally as 10.

Referring to FIG. 4, the locating and sealing device 10 includes a housing 12. The housing 12 has a first segment 14 and a second segment 16. In the preferred embodiment, the first segment 14 is substantially solid and has an outer diameter in the range of 0.06 inch to 0.20 inch. Three openings 18, 19 and 20 are formed through the first segment 14. The second segment is substantially hollow and preferably has an outer diameter of about 0.5 inch. The first segment has a length of approximately 0.5 inch to 4.0 inches and the second segment has a length of approximately 1.0 inch to 2.0 inches. A flange 22 extends around the periphery of the end of the second segment furthest from the first segment.

A plunger 24 is slidably mounted in the second segment 16 of the housing 12. The plunger 24 has three apertures 26, 27 and 28 formed therethrough. The apertures 26–28 are aligned with the openings 18–20 in the housing 12. A plunger flange 30 is formed around the periphery of one end of the plunger 24. The device 10 can be made of metal or plastic or combinations thereof. Furthermore, while the device has been described with the use of the plunger 24, it may be possible to practice the invention without the plunger by merely extending the main part of the housing 12 rearwardly and likewise extending the openings 18–20.

Tubes 32, 34 and 36 extend through corresponding openings 18, 19 and 20 and corresponding apertures 26, 27 and 28. The tubes preferably have an inner diameter of about 0.008 inch to 0.03 inch and an outer diameter of about 0.013 inch to 0.035 inch. It should be noted that more than one tube can be inserted through each of the opening and aperture combinations.

In the preferred embodiment, stylet 38 or 40 extends from a corresponding one of the apertures 26 and 28 and openings 18 and 20. Each stylet ends in a point 42 and 44, respectively, and preferably has an outer diameter in the range of 0.008 inch to 0.03 inch. Flange projections 46 and 48 extend from the opposite ends of each of the stylets 38 and 40. While the stylets are shown as two separate elements, it should be readily apparent that they can be joined together or formed as one piece and move in unison.

Figure 8:
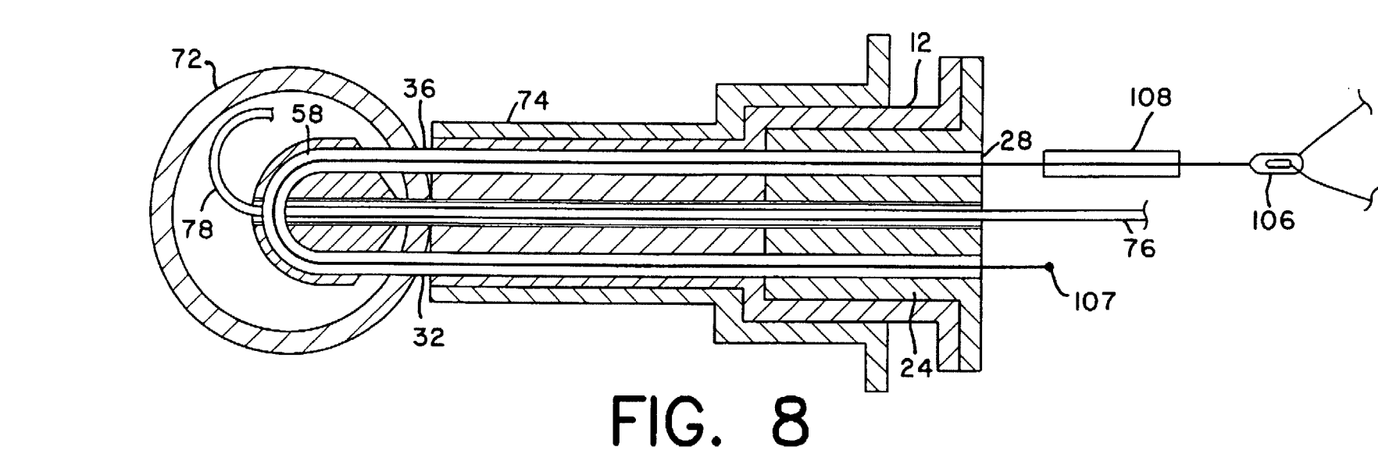
FIG. 8 is a view similar to FIG. 7 showing a suture being inserted through the stylet tubes and suture guide.
Figure 9:
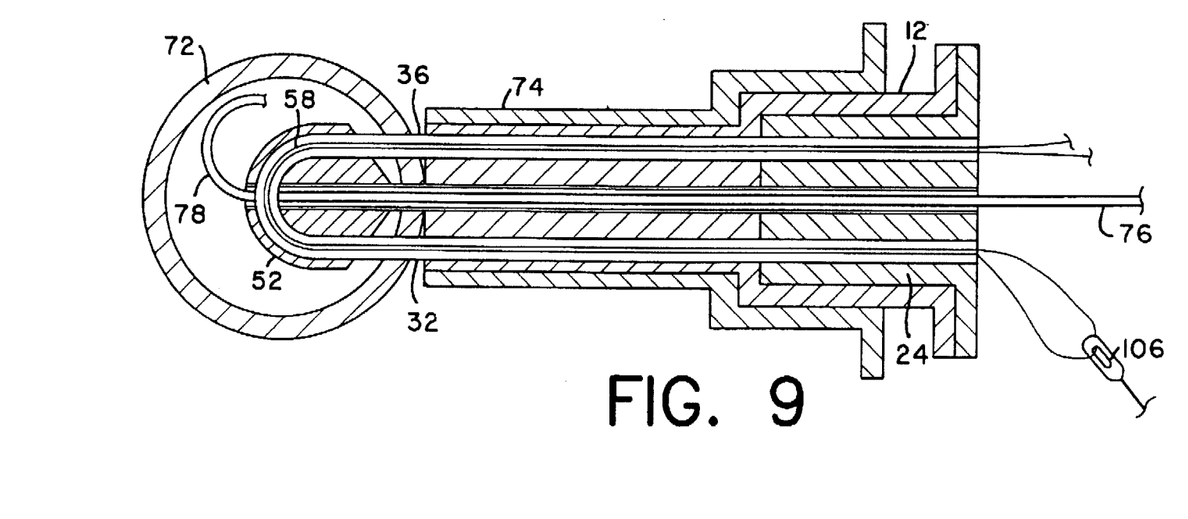
FIG. 9 is a view similar to FIG. 8 showing the suture located within the suture guide.
Figure 10:
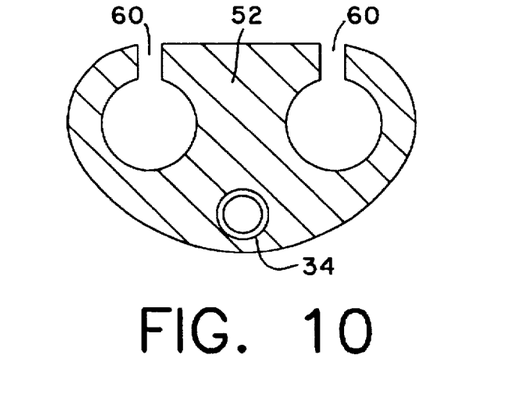
FIG. 10 is a front cross-sectional view of the suture guide taken along lines 10—10 of FIG. 4.
Figure 11:
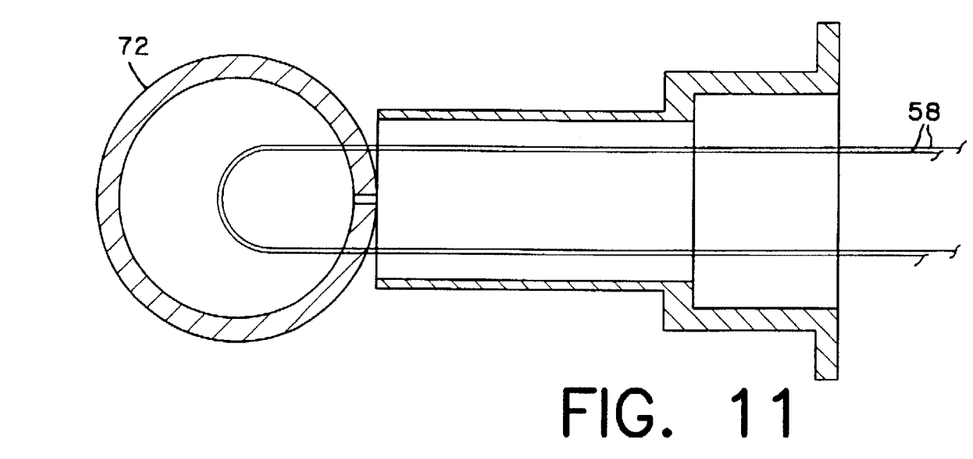
FIG. 11 is a side cross-sectional view showing a suture located within the blood vessel to be closed.

Extending from the end of the first segment 14 of the housing 12 furthest from the second segment 16 is a suture guide 52 which is secured to the distal end of tube 34 which in turn is secured to housing 12. The suture guide 52 has a pair of openings 54 and 56 formed therethrough for receiving a suture 58 as illustrated in FIGS. 8 and 9. A slit 60 is preferably formed in the suture guide 52 in order to facilitate the removal of the device 10 from the suture 58 (see FIG. 10). The suture guide can be made of metal, plastic or rubber.

Figure 1:
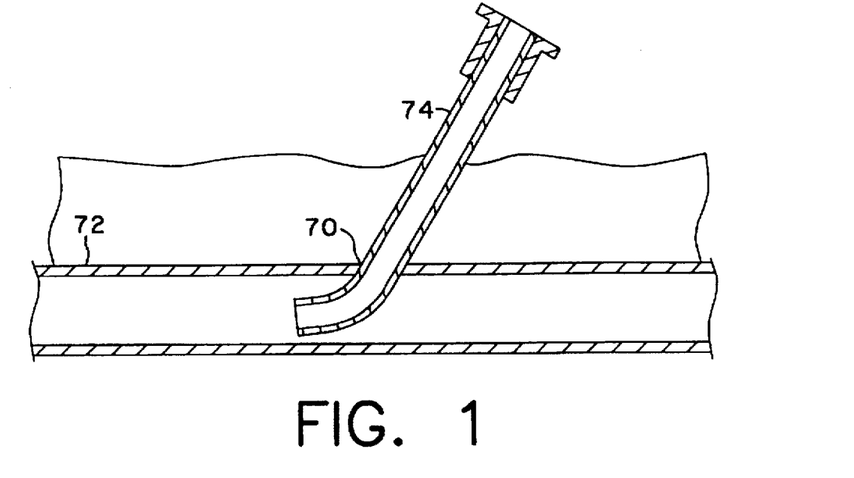
FIG. 1 is a side cross-sectional view showing a procedure sheath extending through a percutaneous puncture in a blood vessel.
Figure 2A:
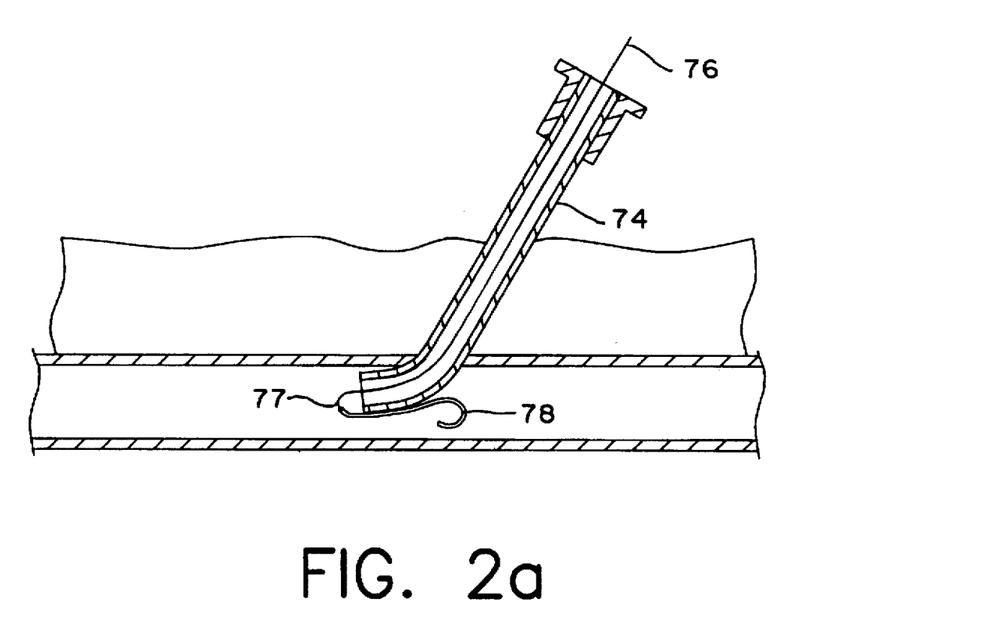
FIG. 2a is a view similar to FIG. 1 showing a guide wire inserted into the procedure sheath.

To facilitate an understanding of the principles of the foregoing apparatus, its operation will now be briefly described. In order to perform an intravascular procedure, a puncture or incision 70 is made in a blood vessel 72 (see FIG. 1). A procedure sheath 74 extends into the puncture. Once the procedure has been carried out, the puncture 70 must be closed. This is accomplished by first inserting a guide wire 76 through the procedure sheath 74 and into the interior of the vessel. The guide wire 76 preferably has one end bent so that there is a reverse bent portion 77 and a J-shaped curved portion 78 as shown in FIG. 2a.

Figure 2B:
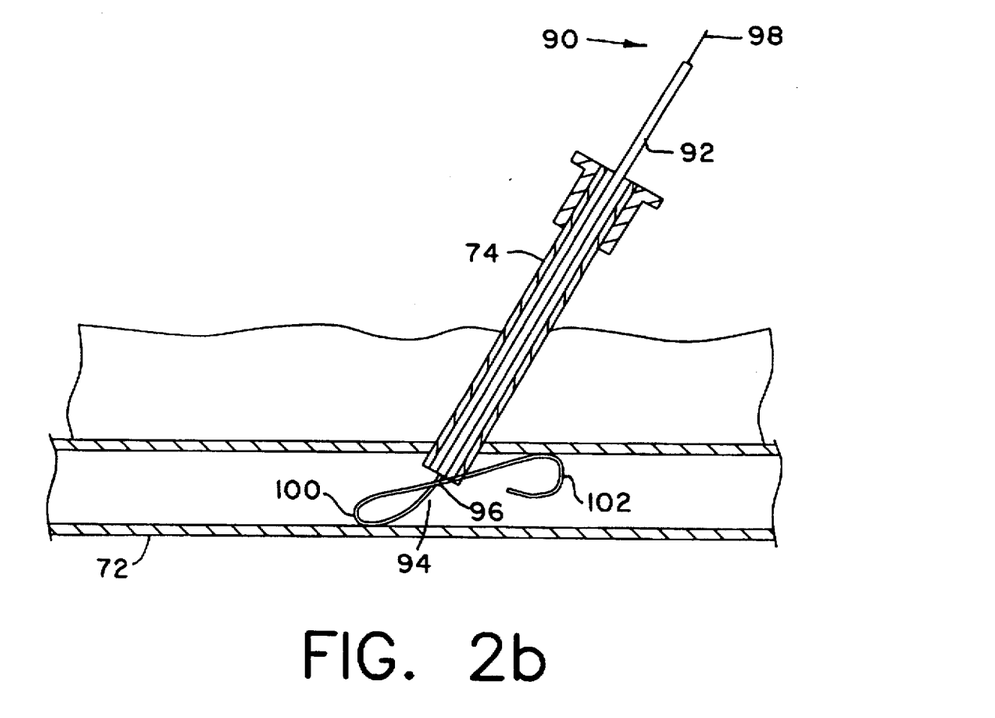
FIG. 2b is a side cross-sectional view of an alternate embodiment for the guide wire.

In the alternate configuration shown in FIG. 2b, the guide wire is replaced with a guide wire assembly 90 which consists of a tube 92 that has a beveled tip 94 with a hole 96 formed therethrough. The guide wire assembly 90 also includes a guide wire 98 that has a reverse bent portion 100 and a J-shaped curved portion 102. The bent portion is formed by inserting the wire 98 through the hole 96 in the tube 92. The guide wire preferably has an outer diameter in the range of 0.008 inch to 0.03 inch and is made of nickel titanium alloy.

Figure 2C:
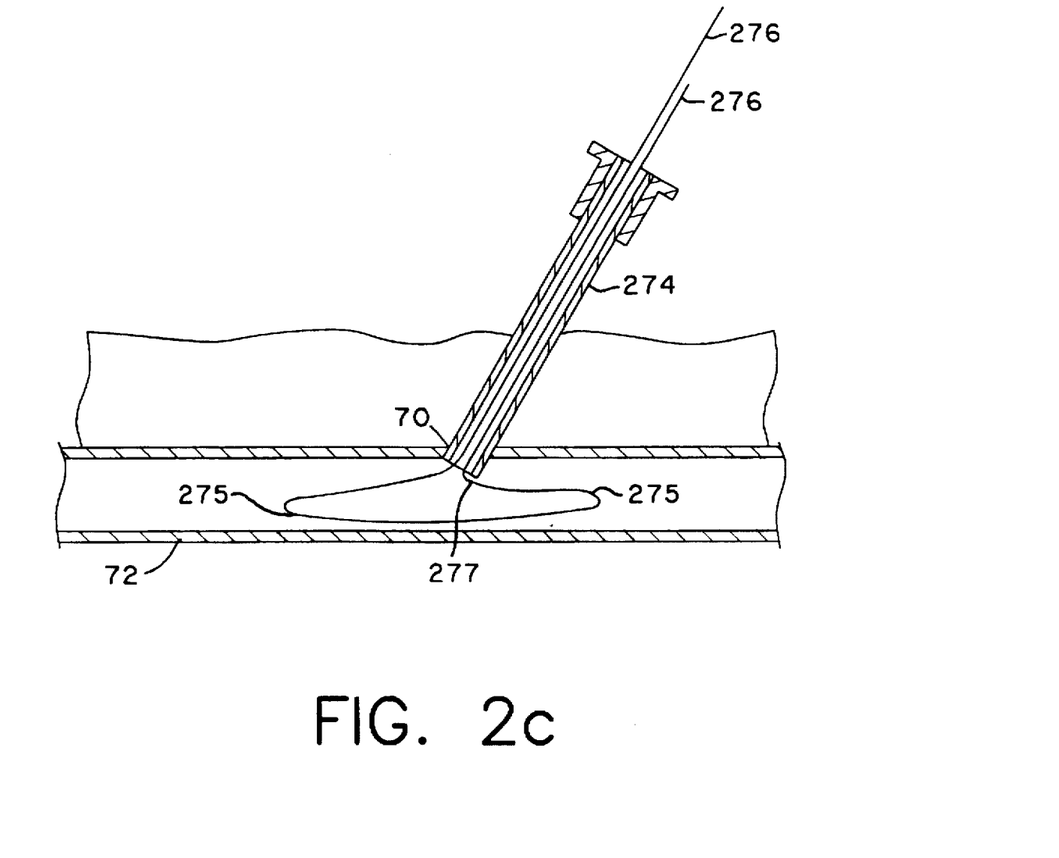
FIG. 2c is a side cross-sectional view of yet another embodiment for the guide wire.

In another configuration shown in FIG. 2c, a guide wire 76 276 is inserted through procedure sheath 274. The guide wire 276 preferably has a curved portion 277 with sides 275. As the curved portion 277 passes through the sheath 274 and into the blood vessel 72, the sides 275 extend outwardly. Accordingly, the sides prevent the guide wire from exiting the blood vessel when the procedure sheath is pulled from the same.

Figure 3:
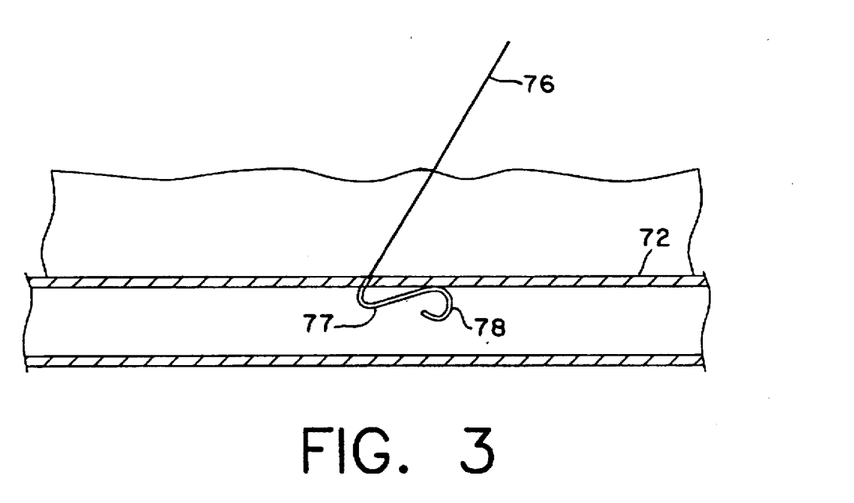
FIG. 3 is a side cross-sectional view showing the guide wire extending through the percutaneous puncture in a blood vessel.

Referring back to FIG. 2a, once the guide wire 76 is inserted into the blood vessel 72, the surgeon begins withdrawing both the procedure sheath 74 and the guide wire. Note, in the alternate configuration shown in FIG. 2b, the tube 92, the sheath 74 and the wire 98 are withdrawn as a unit. The withdrawal of the wire and the sheath continues until resistance is felt. The resistance is caused by the reverse bent portion 77 of the guide wire contacting the vessel wall as shown in FIG. 3. At this point, the sheath is completely removed from the vessel, while the guide wire 76 is left in place.

Figure 6:
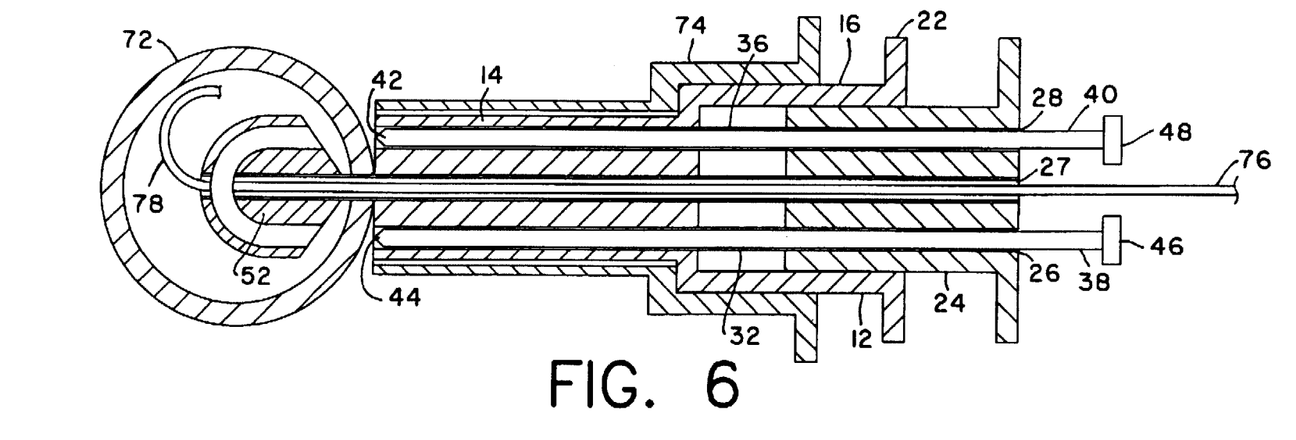
FIG. 6 is a view similar to FIG. 5 showing the same in combination with a guide wire inserted in a blood vessel.

Thereafter, the device 10 is inserted over the guide wire 76. More specifically, the tube 34 is slid over the free end of the guide wire (see FIG. 6). The suture guide 52 is passed through the skin and through the puncture 70 in the vessel while the guide wire is held in place. The device is moved into the vessel until further entry is impeded by the opposing vessel wall and the reverse bent portion 77 of the guide wire 76. Accordingly, the guide wire allows the user of the device 10 to locate the puncture 70 in the vessel.

Figure 7:
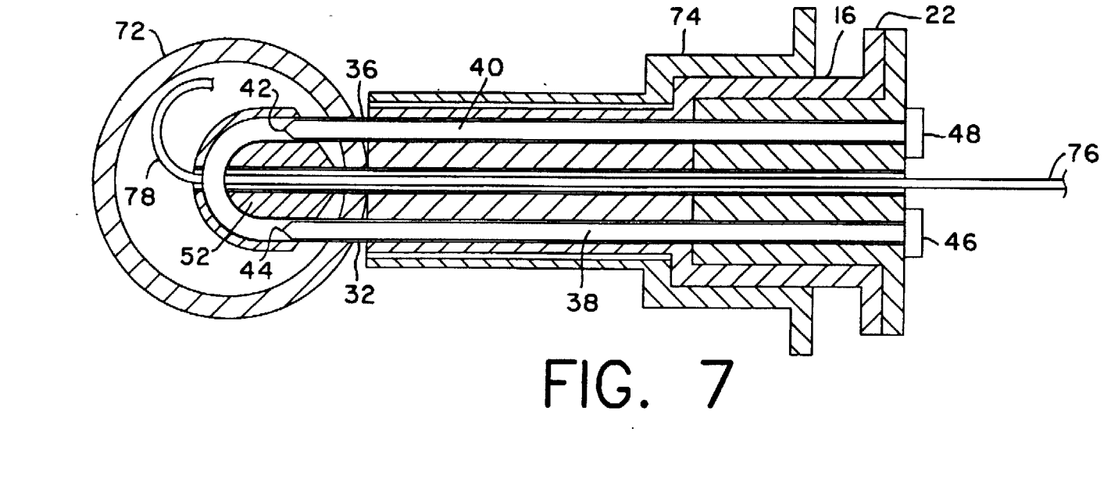
FIG. 7 is a view similar to FIG. 6 showing the stylets and stylet tubes inserted into the suture guide.

The plunger 24 is then pushed toward the vessel until the plunger flange 30 comes into contact with the flange 22 of the housing 12. The stylets 38 and 40 are pushed into their respective tubes 32 and 36 until the pointed tips 42 and 44 pierce the vessel wall at opposite sides of the puncture 70 and engage the openings 54 and 56 in the suture guide 52. Accordingly, the insertion of the pointed tips 42 and 44 create small holes in the vessel. Movement of the stylets into the suture guide causes the tubes 32 and 36 to similarly engage the openings 54 and 56 in the suture guide. It should be noted that the stylets can be eliminated and the suture tubes themselves can have points for piercing the vessel wall.

The stylets 38 and 40 are then entirely removed from the device 10 by grasping the flange portions 46 and 48 and pulling the stylets away from the vessel. Upon removal of the stylets, a suture 58 is fed through tube 36, around suture guide 52, and out tube 32. This is accomplished by first threading the suture 58 through a hole in one end of a suture introducer 106 as illustrated in FIGS. 8 and 9. The suture introducer is preferably a thin flexible rod made of plastic or metal. The opposite end of the suture introducer 106 is then fed through the tube 36, suture guide 52 and tube 32. Thereafter, the end 107 of the suture introducer 106 which extends from tube 32 is pulled away from the plunger 24. This causes the suture 58 to be properly fed through the device 10. In the preferred embodiment, a pusher 108 is fit over the suture introducer 106 in order to facilitate the insertion of the introducer into the device 10 (see FIG. 8).

Figure 12:
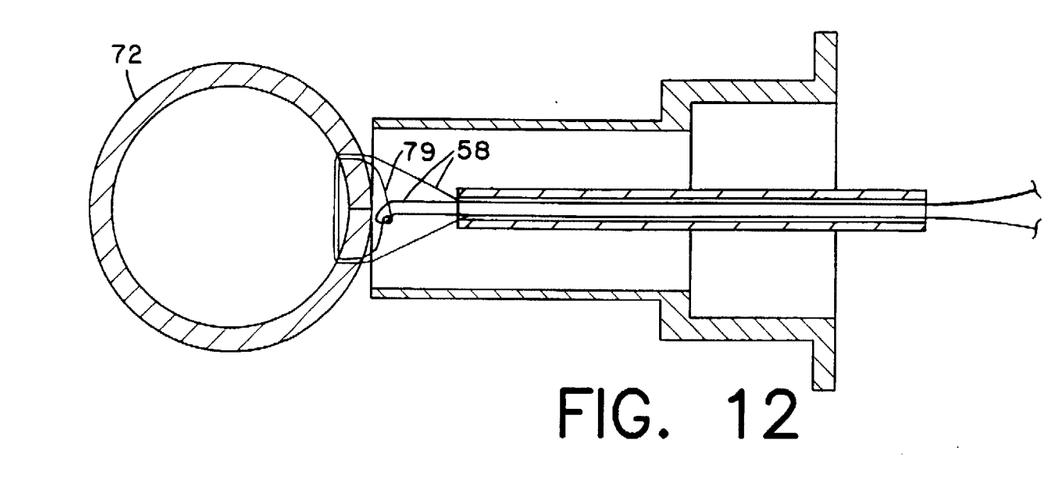
FIG. 12 is a side cross-sectional view showing the suture tied in a knot.

The tubes 32 and 36 are then withdrawn by pulling back on the plunger 24. Thereafter, guide wire 76 is removed. The device 10 is then pulled out of the vessel. As the device is withdrawn from the vessel, the suture guide 52 contacts the middle portion of the suture and causes the same to exit the vessel 72 through the puncture 70. Thereafter, this middle portion of the suture can be manually removed from the suture guide 52 through the slit 60 formed therein. The physician then pulls on the ends of the suture, which extend from the holes in the vessel formed by the pointed tips 42 and 44 of the tubes 32 and 36, until the middle portion re-enters the vessel through the puncture 70. It should be noted that the slit is adapted to slightly expand to allow the suture to readily pass through. A slip knot 79 is then tied on the suture as shown in FIG. 12.

Figure 13:
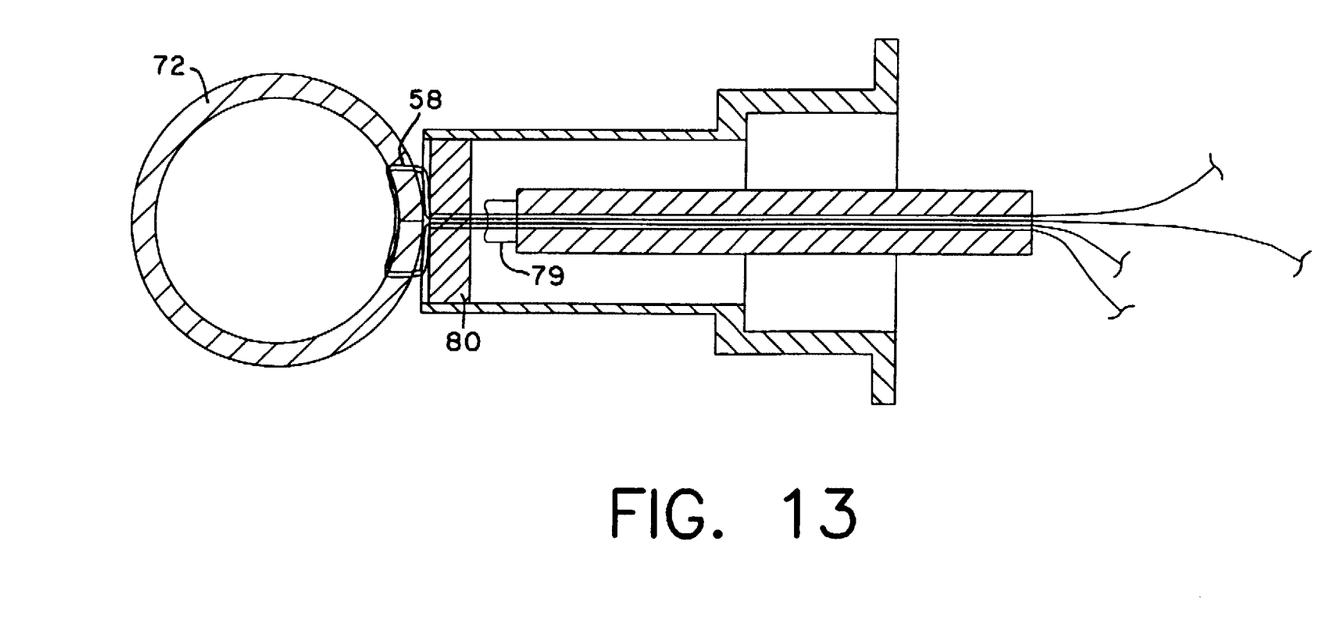
FIG. 13 is a view similar to FIG. 12 but showing the use of hemostatic material.

As shown in FIG. 13, hemostatic material 80 can be threaded onto the suture so that when the knot is slid into place, the hemostatic material comes into contact with the vessel wall in order to facilitate hemostasis. The puncture is then sufficiently sealed.

Figure 14:
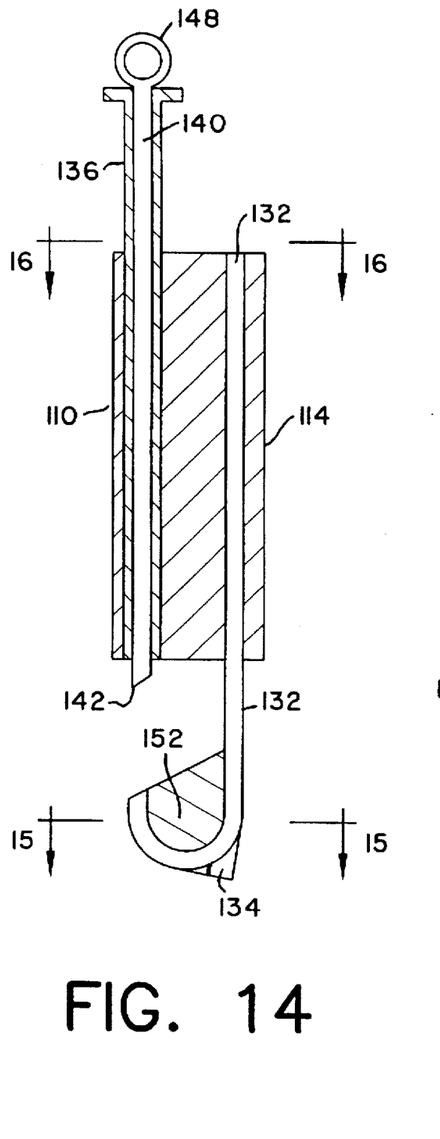
FIG. 14 is a side cross-sectional view of an alternate embodiment of the invention.
Figure 15:
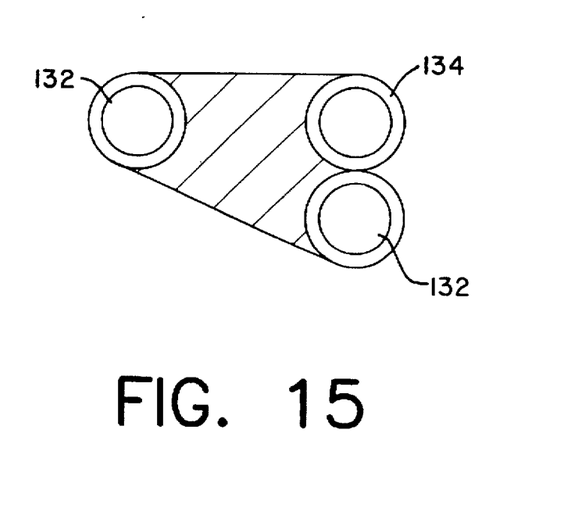
FIG. 15 is a cross-sectional view taken along lines 15—15 of FIG. 14.
Figure 16:
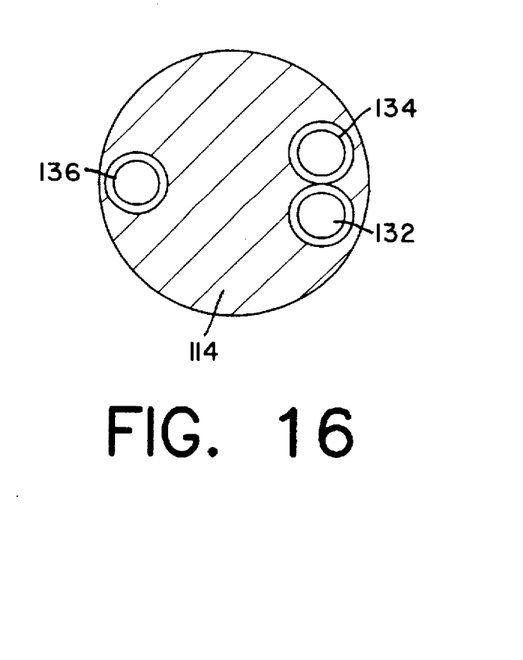
FIG. 16 is a cross-sectional view taken along lines 16—16 of FIG. 14.

Referring to FIGS. 14–16, an alternate embodiment 110 is shown which includes a housing 114 with a plurality of openings formed therethrough. A tube 136 extends through one of the openings and is axially slidable therein. Tubes 132 and 134 extend through the other openings in the housing 114 but are rigidly secured to the same. Extending into tube 136 is a stylet 140 that has a pointed tip 142. A handle portion 148 extends from the free end of the stylet 140. Secured to the lower end of tube 132 is a suture guide 152. The suture guide 152 has a bore 154 formed therethrough which communicates with the end of the tube 132.

The device 110 is used in essentially the same manner as the embodiments discussed above with certain exceptions. A guide wire is first partially inserted into a puncture in a blood vessel as shown in FIG. 3. Tube 134 is then inserted over the portion of the guide wire which extends from the blood vessel. As the tube is moved toward the blood vessel, the suture guide 152 passes through the puncture and into the blood vessel. The operator then grasps the handle portion 148 and pushes the stylet toward the vessel. This causes the pointed tip 142 of the stylet to pierce the blood vessel and causes the tube 136 to be pushed into the free end of the suture guide 152 in communication with the bore 154. The stylet 140 is then removed from the device.

Thereafter, a suture is fed through tube 136, through the bore 154 of the suture guide 152 and out tube 132. The device 110 is then pulled out of the vessel. As the device is withdrawn, the suture exits the suture guide 152 through an elongated slit in the tip thereof. A slip knot is then tied on the suture. It should be noted that the original puncture formed in the vessel, through which the guide wire is inserted, is not closed by the suture. Rather, the suture is used as a guide for placing hemostatic material in contact with the puncture in the blood vessel in order to facilitate hemostasis.

The present invention may be embodied in other forms without departing from the spirit or essential attributes thereof and accordingly reference should be made to the claims rather than to the foregoing specification as indicating the scope thereof.

What is claimed is:

1. A device for sealing a puncture in a blood vessel comprising:

a housing having a plurality of openings formed therethrough, each of the openings extended from a first end of the housing to a second end thereof, the housing including a reception portion at the first end;

a plurality of tubes, each of the tubes extending through a respective one of the openings, wherein the plurality of tubes includes a pair of spaced apart suture tubes and a guide wire tube, each of the tubes extending through a corresponding one of the openings and wherein each of the suture tubes includes a pointed tip for piercing the wall of the blood vessel;

a piercing member associated with a first one of the plurality of tubes;

a suture guide member extending from the second end of the housing for retaining a suture therein;

a support member secured to the suture guide member and extending through the housing from the first end to the second end thereof; and a plunger member slidably positioned in the reception portion of the housing and coupled to the piercing member so that when the plunger member is slidably moved toward the second end of the housing, the blood vessel is pierced by the piercing member.

2. The device of claim 1 wherein the plunger member includes a plurality of apertures extending therethrough, each of the apertures in the plunger member being aligned with a respective one of the openings in the housing.

3. The device of claim 2 wherein guide wire tube is adapted to slide over a guide wire extending through the puncture in the blood vessel.

4. A device for sealing a puncture in a blood vessel comprising:

a housing having a plurality of openings formed therethrough, each of the openings extended from a first end of the housing to a second end thereof, the housing including a reception portion at the first end;

a plurality of tubes, each of the tubes extending through a respective one of the openings;

a piercing member associated with a first one of the plurality of tubes;

a suture guide member extending from the second end of the housing for retaining a suture therein, wherein the suture guide member is coupled to a second one of the tubes; and a plunger member slidably positioned in the reception portion of the housing and coupled to the piercing member so that when the plunger member is slidably moved toward the second end of the housing, the blood vessel is pierced by the piercing member.

* * * * *